US012551616B1

(12) United States Patent
Zagzoog

(10) Patent No.: US 12,551,616 B1
(45) Date of Patent: Feb. 17, 2026

(54) INTERNAL LARYNGEAL MUSCLE INJECTION TOOL

(71) Applicant: Faisal H Zagzoog, Jeddah (SA)

(72) Inventor: Faisal H Zagzoog, Jeddah (SA)

( * ) Notice: Subject to any disclaimer, the term of this patent is extended or adjusted under 35 U.S.C. 154(b) by 0 days.

(21) Appl. No.: 19/238,841

(22) Filed: Jun. 16, 2025

(51) Int. Cl.
*A61M 5/158* (2006.01)
*A61L 31/06* (2006.01)

(52) U.S. Cl.
CPC ............. *A61M 5/158* (2013.01); *A61L 31/06* (2013.01); *A61M 2210/1028* (2013.01)

(58) Field of Classification Search
CPC .......... A61M 5/158; A61M 2210/1028; A61L 31/06
USPC .......................................................... 604/511
See application file for complete search history.

(56) References Cited

U.S. PATENT DOCUMENTS 9,700,408 B1 * 7/2017 Sataloff ..................... A61F 2/20
2004/0254642 A1 * 12/2004 Isshiki ...................... A61F 2/20 623/9
2020/0085570 A1 * 3/2020 Ho ............................ A61F 2/20

* cited by examiner

*Primary Examiner* — Phillip A Gray
(74) *Attorney, Agent, or Firm* — WCF IP

(57) ABSTRACT

A silicone implant is fixed onto the thyroid cartilage and the implant has a guide channel extending therethrough. The placement allows fixation to the cartilage by blade portions on opposite sides of the implant, with the guide channel being positioned in front of the muscles to be treated. The implant enables safe, accurate, and repeatable injections into internal laryngeal muscles under local anesthesia, and simplifies surgical access, increases accuracy, and reduces risks associated with traditional techniques.

2 Claims, 5 Drawing Sheets

INTERNAL LARYNGEAL MUSCLE INJECTION TOOL

CROSS-REFERENCE TO RELATED APPLICATIONS

This application claims priority to Saudi Arabian Patent Registration No. SA 1020250499 filed on Jan. 22, 2025, and the complete contents thereof is herein incorporated by reference.

FIELD OF THE INVENTION

This invention generally relates to a device for facilitating precise, safe, and repeatable injections into the internal laryngeal muscles via surgical fixation on the thyroid cartilage, as well as to the treatment of vocal or laryngeal muscle disorders.

BACKGROUND

Injection therapy into internal laryngeal muscles is a common approach for managing voice and mobility impairments such as paralysis, weakness, tremors, or neurogenic speech disorders. Conventional methods are challenging due to the anatomy. One conventional method involves endoscopic procedures under general anesthesia. The requirement of anesthesia poses costs and possible anesthesia-related complications. Furthermore, the endoscopic procedure itself risks airway trauma. Another conventional method involves percutaneous electromyography (EMG) guided injections. These are performed blindly or under EMG, with risks of misplacement, airway compromise, and injury to surrounding tissues. These two conventional approaches are technically demanding, uncomfortable for the patient, and often require repeated anesthesia sessions.

US Patent Publication 2020/0085570 to Ho describes an implant system and method for treating glottic insufficiency that includes a fixation frame for securing the implant system to the patient's thyroid cartilage. The system is complex and includes an inflatable flexible member that is configured to push against the artenoid cartilage. The Ho device is designed for use only unilateral vocal fold insufficiency patients, and is not fit for tissue injection as its function is to mechanically push using the implanted balloon member. Moreover, the Ho device uses metal components and requires screws and sutures for placement.

A need exists for a device that allows safe, accurate, and repeatable injections directly into target muscles in the throat.

SUMMARY

The invention provides a surgically implantable silicone device that attaches firmly to the thyroid cartilage, creating a stable conduit enabling repeated injections into internal laryngeal muscles under local anesthesia. It includes a guide channel, fixation blades, and a protruding ring for localization during surgery. This device simplifies access, reduces risks, and improves accuracy.

The internal laryngeal muscle injection tool will allow injecting botox, steroid, and filler or other material to the glottic and para glottic space for treatment purposes. It enables delivery of the material to the exact required site, allowing it to be absorbed by the muscle. In many treatment methods, repeated injections may take place under local anesthesia.

The invention is designed to provide direct access through the thyroid cartilage at the level of the vocal folds. This allows the passage of a needle to inject material to the exact vertical level of the vocal folds. In a particular embodiment, a double vertical window is provided in order to allow needle passages to two different levels. For example, in this particular embodiment one access point can be positioned at the level of the true vocal fold, while another access point can be positioned at the level of the false vocal fold, which is higher up from the vocal fold.

The invention provides treatment benefits to patients who having a variety of different conditions including without limitation aDductor spasmodic dysphonia, aBductor spasmodic dysphonia, vocal fold paralysis, vocal fold insufficiency, vocal fold scar, vocal fold sulcus muscle tension dysphonia, irritable larynx syndrome, vocal fold nodules, and vocal fold polyps.

DETAILED DESCRIPTION

Figure 1:
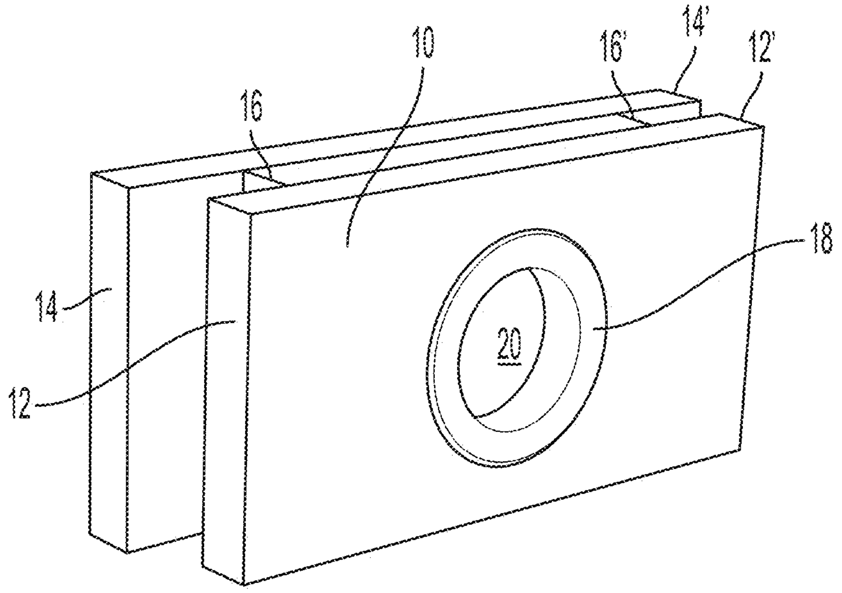
FIG. 1 is an isometric view of an embodiment of the internal laryngeal muscle injection tool.

With reference to FIG. 1, the internal laryngeal muscle injection tool 10 is almost flat in appearance, and has blades 12 and 12' on opposite sides of its front surface and blades 14 and 14' on opposite sides of its rear surface. The pair of blades 12 and 14, or 12' and 14' are separated respectively by spacers 16 and 16'. An opening 18 is preferably raised above the surface that will face away from the subject's throat, and will include an opening 20 through which needles can pass through the internal laryngeal muscle injection 10. The opening 20 can include a mesh material of silicone functioning to provide protection to the glotic and paraglotic spaces, and serve as a support for skin and other tissue overgrowth after implantation.

The internal muscle injection tool 10 has an external surface which faces away the subject's throat, and which is shown in FIG. 1, and an internal surface which faces inward into the subject's throat which is positioned inside the cartilage opposite the target muscles. Preferably the entire device 10 is made of medical grade silicone, such as specification 45A. The protruding ring 18 on the external surface is used during surgery for localization and alignment of the guide channel. The opening 20 functions as the needle passage channel and can basically be a conduit constructed from medical silicone, such as specification 15A, and connects the outside of the device 10 into the internal space in alignment with the target muscles. The fixation blades 12, 12', 14, and 14' are designed to secures the device 10 onto the thyroid cartilage as discussed in more detail with FIGS.

2 and 3. The spacers 16 and 16' function as cartilage fixation cavities. Cartilage from a window (e.g. approximately 5 mm by 5 mm or other suitable size) fits between the pairs of blades 12 and 14, and 12' and 14', and into the spacer 16 and 16' regions.

Figure 2:
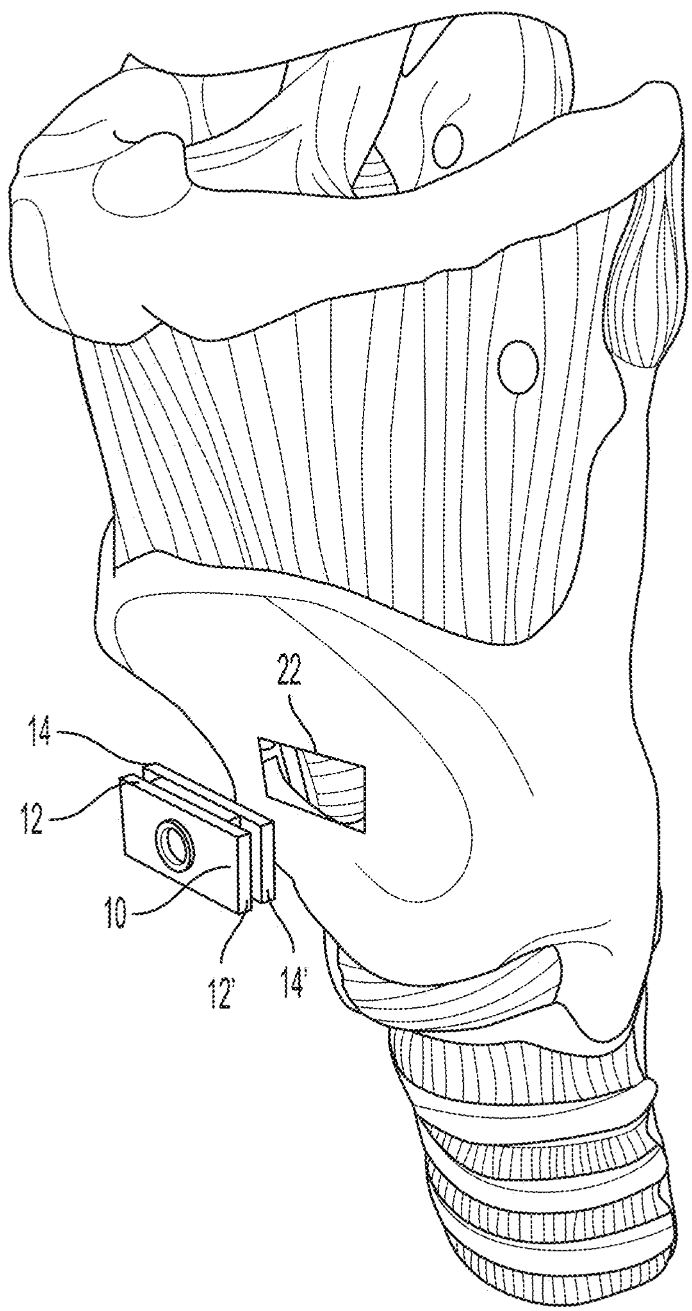
FIG. 2 illustrates the process of implanting the internal laryngeal muscle injection tool in the thyroid cartilage.

FIG. 2 shows that during surgical implantation, under local anesthesia, an anterior neck incision is made at the level of the thyroid cartilage. A square or rectangular segment in the cartilage is excised to make an opening 22 therein. This could be accomplished, for example, with a 15 mm surgical blade. The size of the opening 22 and its location in the cartilage will depend on what is to be treated. The objective is to provide an opening 22 which is aligned with thyroid muscles or other tissues which will absorb material injected through the device 10 after implantation. The size of the segment removed will leave an opening 22 wherein portions of the cartilage on either side of the opening 22 will fit within the spacers 16 and 16'. This allows the blades 12 and 12' to rest on cartilage externally at the anterior site, and the blades 14 and 14' to rest on cartilage internally at the anterior site. The length of over lap of the blades 12 and 14 with cartilage therebetween in spacer 16, and the overlap of the blades 12' and 14' with cartilage in spacer 16' should be sufficient to fix the device 10 to the cartilage without other fixation devices, such as sutures and screws. However, surgical adhesive may be added within the spaces 16 and 16' to assure adhesion. The location chosen for forming the opening 22 is such that when the device 10 is implanted it forms a stable attachment to the cartilage with the guide channel 20 aligned with the target muscles.

Figure 3:
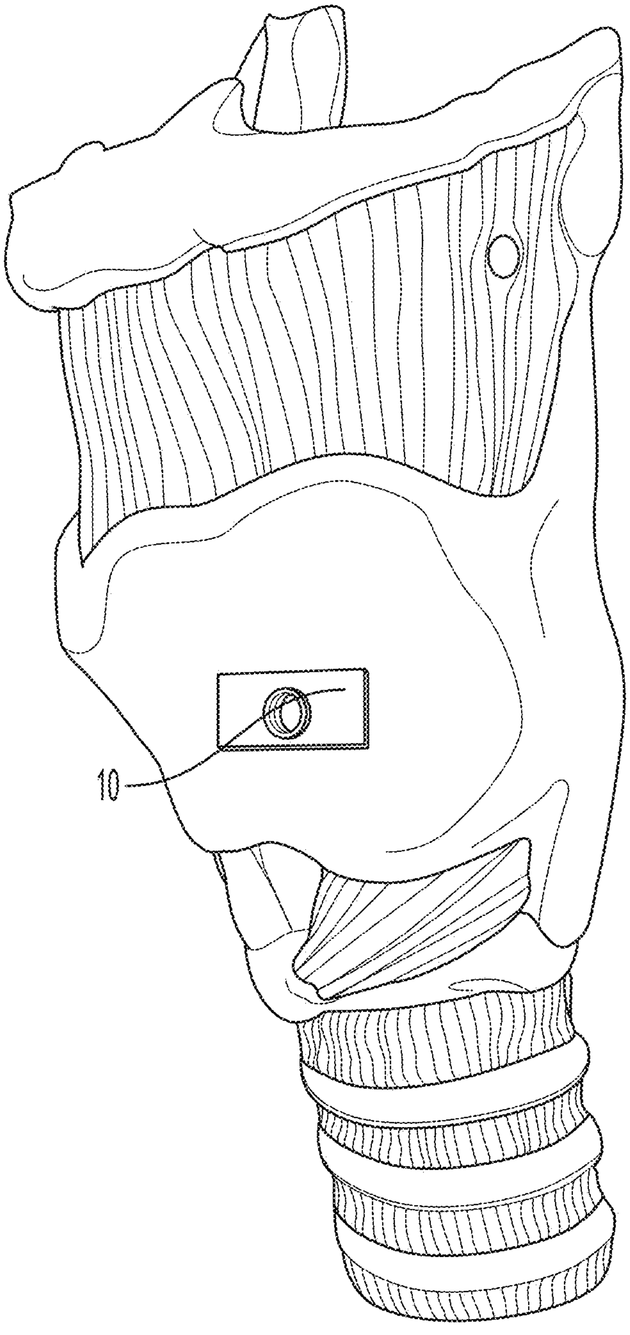
FIG. 3 illustrates the internal laryngeal muscle injection tool implanted in the thyroid cartilage.

FIG. 3 shows the internal laryngeal muscle injection tool 10 secured to the cartilage in the opening 22 (FIG. 2). The relatively flat design of the tool 10 enables it to fit neatly under the skin on the exterior surface, and to occupy very little volume on the interior surface.

Figure 4:
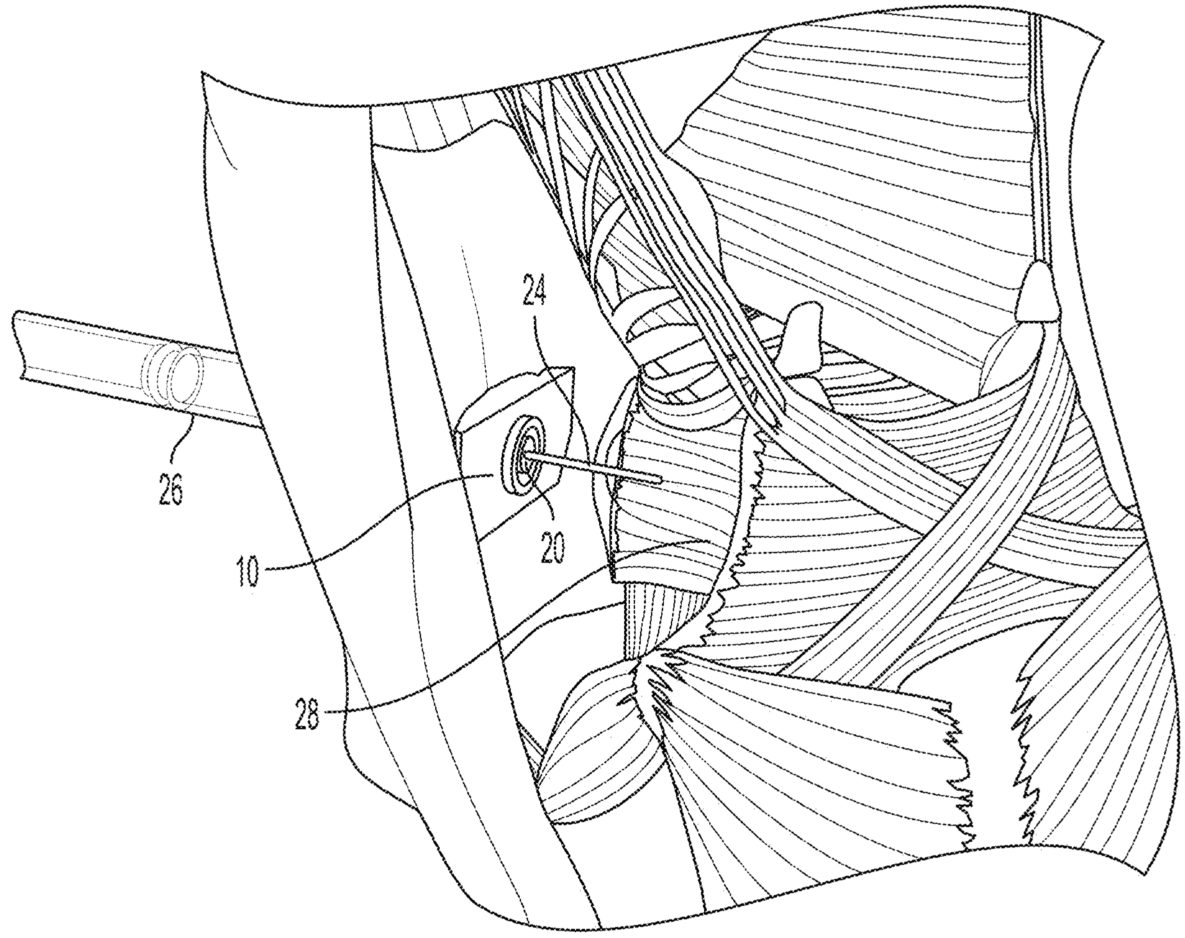
FIG. 4 is a reverse view showing an end of injection needle delivering material to the glottic and para glottic space for treatment purposes, whereby the opening for the needle in the internal laryngeal muscle injection tool enables delivery of the material to the exact required site, allowing it to be absorbed by the muscle.

FIG. 4 shows that, in use, the end of a needle 24 extends through the opening 20 in the internal laryngeal muscle injection tool 10 to deliver medication or other material from the syringe 26 to the muscles 28 of interest that are in alignment with the opening 20. The fixation blades 12, 12', 14, and 14' (FIG. 1) hold the device 10 in place so that injections may be made repeatedly over time to the muscles 28 of interest. The internal laryngeal muscle injection tool 10 can be used in the treatment plan for a variety of different conditions including limitation aDductor spasmodic dysphonia, aBductor spasmodic dysphonia, vocal fold paralysis, vocal fold insufficiency, vocal fold scar, vocal fold sulcus muscle tension dysphonia, irritable larynx syndrome, vocal fold nodules, and vocal fold polyps. The material delivered from the syringe 26 can be wide ranging including botox, steroids, filler and other material, and will depend upon the condition and the treatment plan.

Once implanted, the therapy for a patient may include delivery of local anesthesia during outpatient follow up visits. Then, a 23G syringe introduces the injection agent (e.g., botulinum toxin) through the guide channel, passing from outside into the target muscles. The needle is guided safely and accurately into the muscles, delivering the therapeutic agent.

Figure 5:
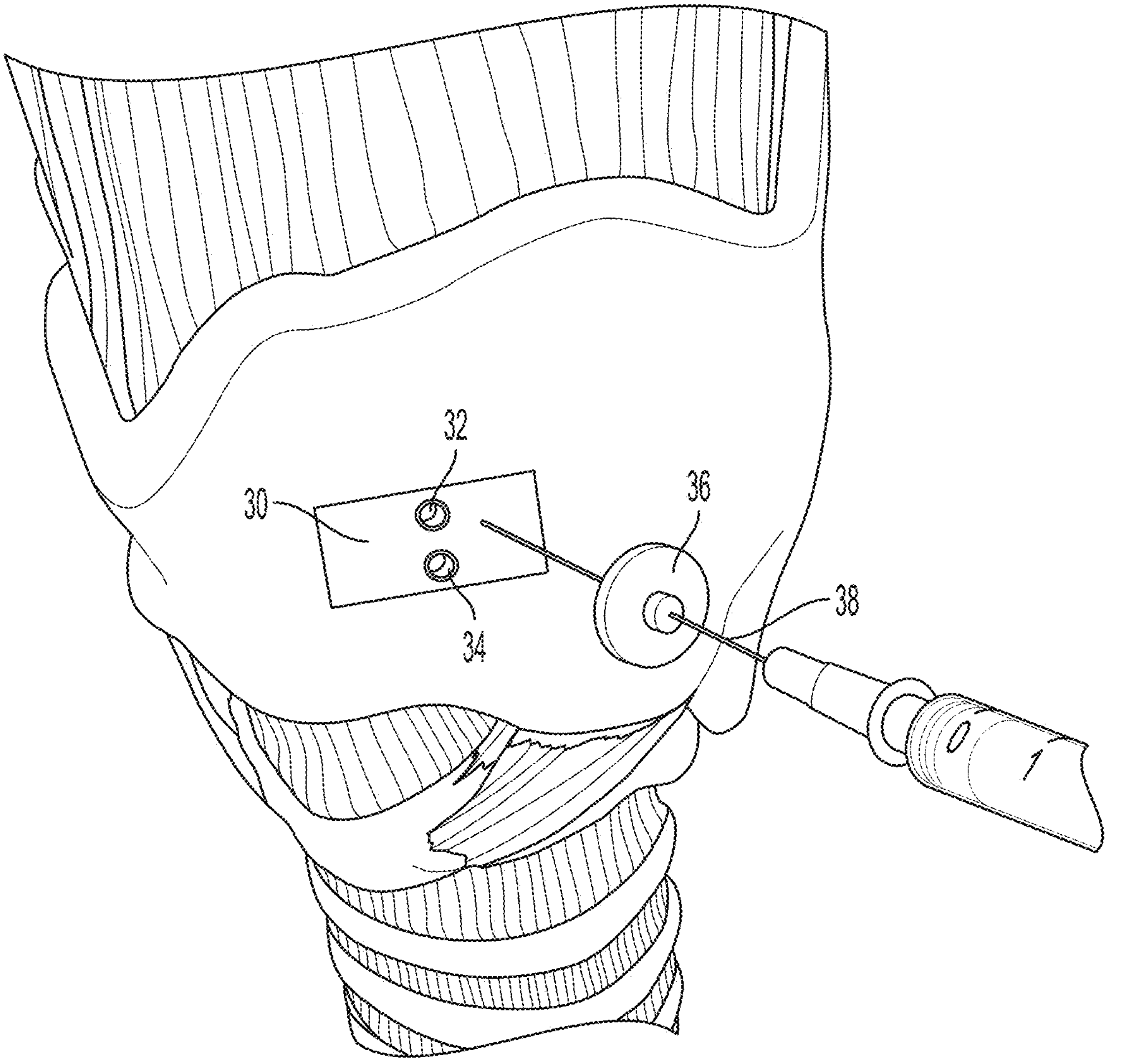
FIG. 5 is another embodiment of the internal laryingeal muscle injection tool which provides access openings for two different delivery sites, such as the vocal fold and the false vocal fold.

FIG. 5 shows an alternative embodiment where the internal muscle injection tool 30 has a plurality of guide openings 32 and 34, but is similar to the tool 10 shown in FIG. 1 in all other respects. This allows delivery of different materials to different spaced apart muscle groups. For example, one opening 34 could be aligned true vocal fold, while the other opening 32 could be positioned higher up at the level of the false vocal fold.

FIG. 5 also shows a safety guard 36 can be used on the needle 38 to prevent insertion at too great a depth that the needle end might contact the muscles underlying the cartilage.

While the guide channels on the internal muscle injection tool are illustrated as circular, they may be any geometric shape including square, hexagonal, etc. While the silicone body of the device 10 and 30 is illustrated as generally rectangular or square, the silicone body may assume any geometric shape including an amorphous shape. Furthermore, while the size of the silicone body of the device 10 and 30 for guiding injections into internal laryngeal muscles has been described as approximately 5 mm×5 mm, this can vary depending on the nature of where the device might be placed (e.g., it could range from 3-10 mm on a side, etc.). While the guide channels 20, 32, and 34 are shown as being circular having a size of 0.5 to 2.0 mm in diameter, they can be of of varying sizes depending on the application. While the guide channels 20, 32, and 34 are preferably filled with a silicone material that is more easily penetrable by a needle than the body 10 or 30, a variety of different materials may be used. Furthermore, while the blades 12, 12', 14, and 14' are shown as projecting from the opposite sides of the silicone body of the device 10 and 30, by 0.5 to 1.5 mm, they length they project can vary depending on the application. Finally, the spacing 16 and 16' between the blades may vary from 0.1-1 mm or more.

Example

Below are the technical specifications for an exemplary laryngeal muscle injection tool 10 as depicted in FIG. 1.

Technical specs of 45A silicone (whole device body made from that material)

| Property | Typical Value | Test Standard |
|---|---|---|
| Material Type | Platinum-cured silicone elastomer | — |
| Form | LSR (Liquid Silicone Rubber)/ HCR (Solid Rubber) | — |
| Color | Translucent (custom pigments optional) | — |
| Shore A Hardness | 45 ± 5 | ASTM D2240 |
| Tensile Strength | 7.5-10 MPa | ASTM D412 |
| Elongation at Break | 400-650% | ASTM D412 |
| Tear Strength | 20-30 kN/m (or ~120-170 ppi) | ASTM D624 |
| Compression Set | ≤30% (22 hrs @ 175° C.) | ASTM D395 |
| Density | 1.12-1.15 g/cm$^3$ | ASTM D792 |
| Resilience | Moderate to High | — |
| Operating Temperature | −55° C. to +200° C. | — |
| Water Absorption (24 h) | <0.1% | ASTM D471 |
| Cure System | Addition (Platinum) Cure | |

Technical specs of 15A silicone (the window made from that material)

| Property | Typical Value | Test Method |
|---|---|---|
| Type | Platinum-cured medical-grade silicone | — |
| Hardness (Shore A) | 15 | ASTM D2240 |
| Color | Transparent or translucent (can be tinted) | — |

-continued

| Technical specs of 15A silicone (the window made from that material) | | |
|---|---|---|
| Property | Typical Value | Test Method |
| Tensile Strength | 5-8 MPa | ASTM D412 |
| Elongation at Break | 700%-1000% | ASTM D412 |
| Tear Strength | 15-25 kN/m (or 85-145 ppi) | ASTM D624 |
| Compression Set | ≤35% (22 hrs @ 175° C.) | ASTM D395 |
| Density | ~1.1-1.2 g/cm$^3$ | ASTM D792 |
| Operating Temperature | −50° C. to +200° C. | — |
| Biocompatibility | USP Class VI/ISO 10993 certified | USP/ISO Standards |
| Cure System | Addition (Platinum) Cure | — |
| Sterilization Compatibility | Autoclave, EtO, Gamma, E-beam | — |
| Transparency | High (unless filled or pigmented) | Visual |
| Water Absorption | <0.1% | ASTM D471 |
| Extractables & Leachables | Ultra-low, medical grade | USP <87>, <88>, ISO 10993 |

The invention claimed is:

1. A method for surgically preparing a subject in need thereof to receive injections into internal laryngeal muscles in said subject, comprising:

providing a device for guiding injections into internal laryngeal muscles, comprising:

a silicone body with external and internal surfaces;

pairs of spaced apart fixation blades extending from opposite sides of the silicone body, wherein the pairs of spaced apart fixation blades are configured to affix the silicone body to thyroid cartilage of a subject with portions thyroid cartilage passing between the pairs of spaced apart fixation blades;

at least one guide channel extending from the external face to the internal face of the silicone body, wherein the at least one guide channel comprises a plurality of guide channels; and implanting the device in an anterior site in the throat of the subject such that a first of the plurality of guide channels is in alignment with a first selected internal laryngeal muscle area such that multiple injections may be delivered to the first selected internal laryngeal muscle area through the first of the plurality of guide channels, and such that a second of the plurality of guide channels is in alignment with a second selected internal laryngeal muscle area different from and spaced apart from the first selected internal laryngeal muscle area such that multiple injections may be delivered to the second selected internal laryngeal muscle area through the second of the plurality of guide channels.

2. A method for treating the throat of a subject in need thereof, comprising preparing the subject according to claim 1; and repeatedly over time injecting a first material to the first selected internal laryngeal muscle area through the first of the plurality of guide channels; and repeatedly over time injecting a second material different from the first material to the second selected internal laryngeal muscle area through the second of the plurality of guide channels.

* * * * *